(12) United States Patent
Godshalk et al.

(10) Patent No.: US 7,164,105 B2
(45) Date of Patent: Jan. 16, 2007

(54) NON-INVASIVE MICROWAVE ANALYSIS SYSTEMS

(75) Inventors: Edward M Godshalk, Newberg, OR (US); Timothy Raynolds, Woodstock, VT (US); Paul M. Meaney, Hanover, NH (US); Keith D. Paulsen, Hanover, NH (US); Greg Burke, W. Canaan, NH (US)

(73) Assignee: Microwave Imaging Systems Technologies, Inc., Hanover, NH (US)

( * ) Notice: Subject to any disclaimer, the term of this patent is extended or adjusted under 35 U.S.C. 154(b) by 0 days.

(21) Appl. No.: 11/080,726

(22) Filed: Mar. 15, 2005

(65) Prior Publication Data

US 2005/0203387 A1 Sep. 15, 2005

Related U.S. Application Data

(63) Continuation-in-part of application No. 10/407,886, filed on Apr. 4, 2003.
(60) Provisional application No. 60/638,005, filed on Dec. 21, 2004, provisional application No. 60/553,623, filed on Mar. 15, 2004, provisional application No. 60/370,366, filed on Apr. 5, 2002.

(51) Int. Cl.
*H05B 6/64* (2006.01)
*A61B 5/05* (2006.01)

(52) U.S. Cl. .................................. 219/679; 600/430

(58) Field of Classification Search ............. 219/679, 219/601, 680, 678; 600/430, 407; *A05B 6/64; A61B 5/05*
See application file for complete search history.

(56) References Cited

U.S. PATENT DOCUMENTS

| | | | | |
|---|---|---|---|---|
| 5,715,819 | A * | 2/1998 | Svenson et al. | 600/425 |
| 6,004,123 | A * | 12/1999 | Buckley et al. | 425/174.4 |
| 6,332,087 | B1 * | 12/2001 | Svenson et al. | 600/407 |
| 6,490,471 | B1 * | 12/2002 | Svenson et al. | 600/407 |
| 6,686,573 | B1 * | 2/2004 | Behnke et al. | 219/679 |
| 2002/0065463 | A1 * | 5/2002 | Svenson et al. | 600/430 |
| 2002/0088798 | A1 * | 7/2002 | Behnke et al. | 219/679 |

* cited by examiner

*Primary Examiner*—Daniel Robinson
(74) *Attorney, Agent, or Firm*—Lathrop & Gage LC

(57) ABSTRACT

Non-invasive microwave analysis systems and methods determine scattered phase data for a liquid in a container. A transmitter antenna situated within coupling liquid separated from the container by a flexible membrane transmits microwaves that scatter from the container and the liquid in the container. One or more receiver antennas within the coupling liquid convert the microwaves into microwave electronic signals that are processed to determine the scattered phase data.

Non-invasive microwave analysis systems and methods image a portion of a biological subject. A transmitter antenna situated within coupling liquid separated from the subject by a flexible membrane transmits microwaves that scatter from the container and the subject. One or more receiver antennas within the coupling liquid convert the microwaves into microwave electronic signals that are processed to reconstruct a cross-sectional image of the subject.

7 Claims, 17 Drawing Sheets

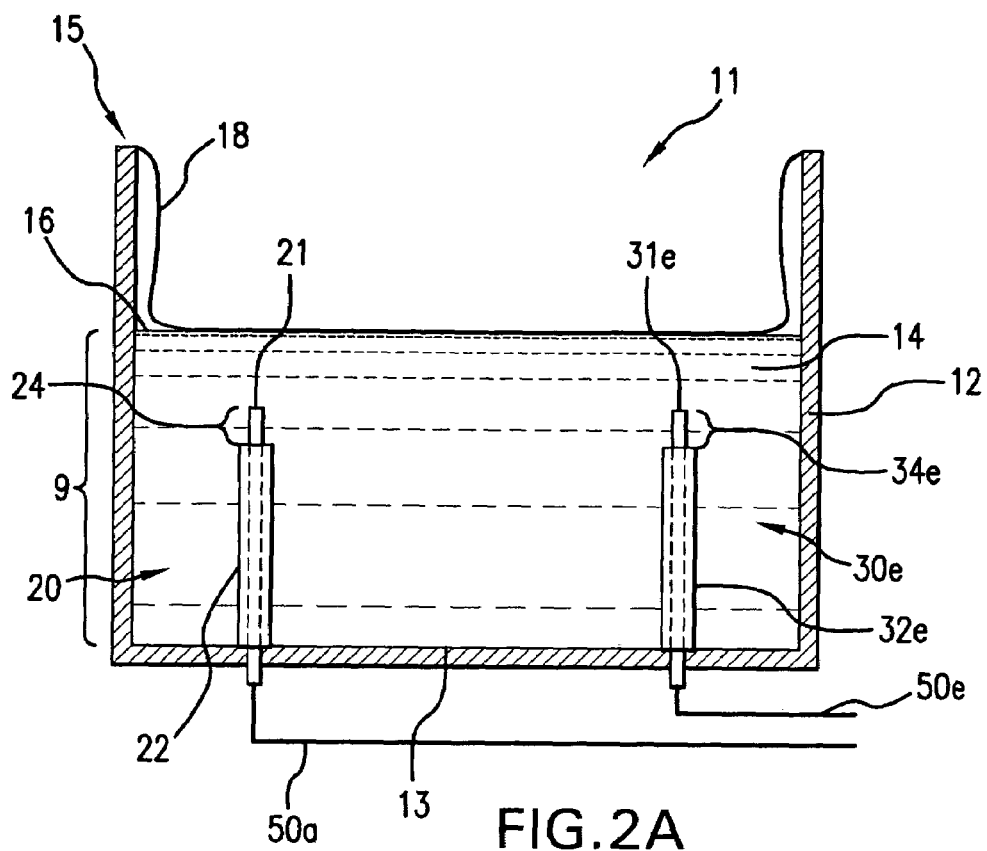
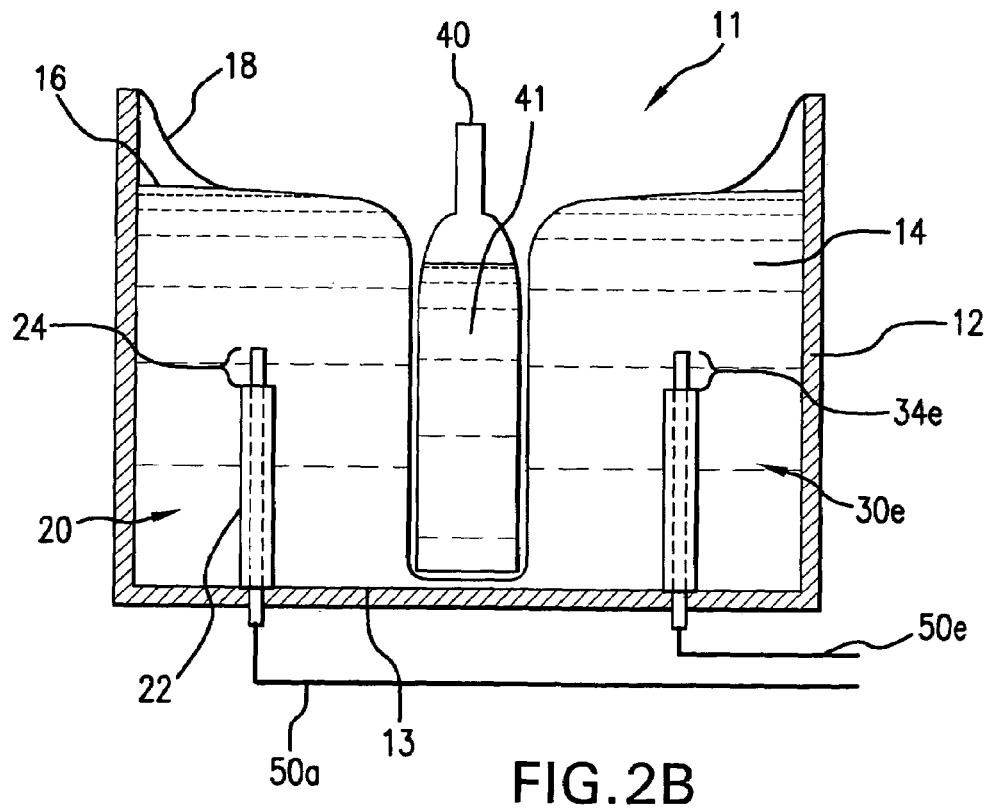

NON-INVASIVE MICROWAVE ANALYSIS SYSTEMS

CROSS-REFERENCE TO RELATED APPLICATIONS

This application claims the benefit of priority of U.S. Provisional Patent Applications No. 60/553,623, filed 15 Mar. 2004, and No. 60/638,005, filed 21 Dec. 2004. This application is also a continuation-in-part of commonly-owned and copending U.S. patent application Ser. No. 10/407,886, filed 04 Apr. 2003, which claims the benefit of priority of U.S. Provisional Patent Application No. 60/370,366, filed 5 Apr. 2002. All of the above-mentioned applications and U.S. Pat. Nos. 6,448,788 and 5,841,288 are incorporated herein by reference.

BACKGROUND

Since Sep. 11, 2001, the United States government and airports have added significantly to the list of items forbidden aboard aircraft, for fear of their use as weapons of terrorism. However, numerous items usually considered harmless are still allowed onto airplanes, some of which can become weapons in the hands of a terrorist. A potential weapon that remains an allowable carry-on item is a container of flammable liquid disguised in an ordinary wine or water bottle. Current X-ray scanners do not distinguish between bottles containing such substances, and bottles containing drinkable liquids. Consequently, the testing of liquids within containers may not occur, primarily because of difficulties or costs associated therewith, including: (1) many passengers would view opening bottles for inspection as intrusive, and (2) direct testing of bottle contents would require stocking of reagents or other test media, and subsequent disposal of tested samples.

SUMMARY

In one embodiment, a non-invasive microwave analysis system determines scattered phase data for a liquid in a container. A transmitter antenna situated within coupling liquid separated from the container by a flexible membrane transmits microwaves that scatter from the container and the liquid in the container. One or more receiver antennas within the coupling liquid convert the microwaves into microwave electronic signals that are processed to determine the scattered phase data.

In one embodiment, a non-invasive microwave analysis system images a portion of a biological subject. A transmitter antenna situated within coupling liquid separated from the subject by a flexible membrane transmits microwaves that scatter from the container and the subject. One or more receiver antennas within the coupling liquid convert the microwaves into microwave electronic signals that are processed to reconstruct a cross-sectional image of the subject.

In one embodiment, a software product includes instructions for determining scattered phase data for a liquid in a container. The software includes instructions for initiating radiation of microwaves from a transmitter antenna within coupling liquid separated from the container by a flexible membrane, and instructions for processing digital signals received from an A–D board corresponding to down-converted IF signals from one or more receiver antennas within the coupling liquid, to determine the scattered phase data.

In one embodiment, a non-invasive microwave screening method includes placing a container of an unknown liquid in a tank. The container is separated by a membrane from coupling liquid in the tank. A failure threshold is generated based on information of the unknown liquid. Microwave radiation transmits from a transmitter antenna situated within the coupling liquid, and scatters from the container and the unknown liquid. One or more receiver antennas situated within the coupling liquid convert the microwave radiation into microwave electronic signals. The microwave electronic signals are processed to determine scattered phase data, which is compared with the failure threshold. A pass result is displayed if the scattered phase data exceeds the failure threshold, but a fail result is displayed if the scattered phase data does not exceed the failure threshold.

BRIEF DESCRIPTION OF THE DRAWINGS

FIG. 2A and FIG. 2B are cross-sectional views of a non-invasive microwave analysis test station, in accord with an embodiment.

DETAILED DESCRIPTION OF THE DRAWINGS

Figure 1:
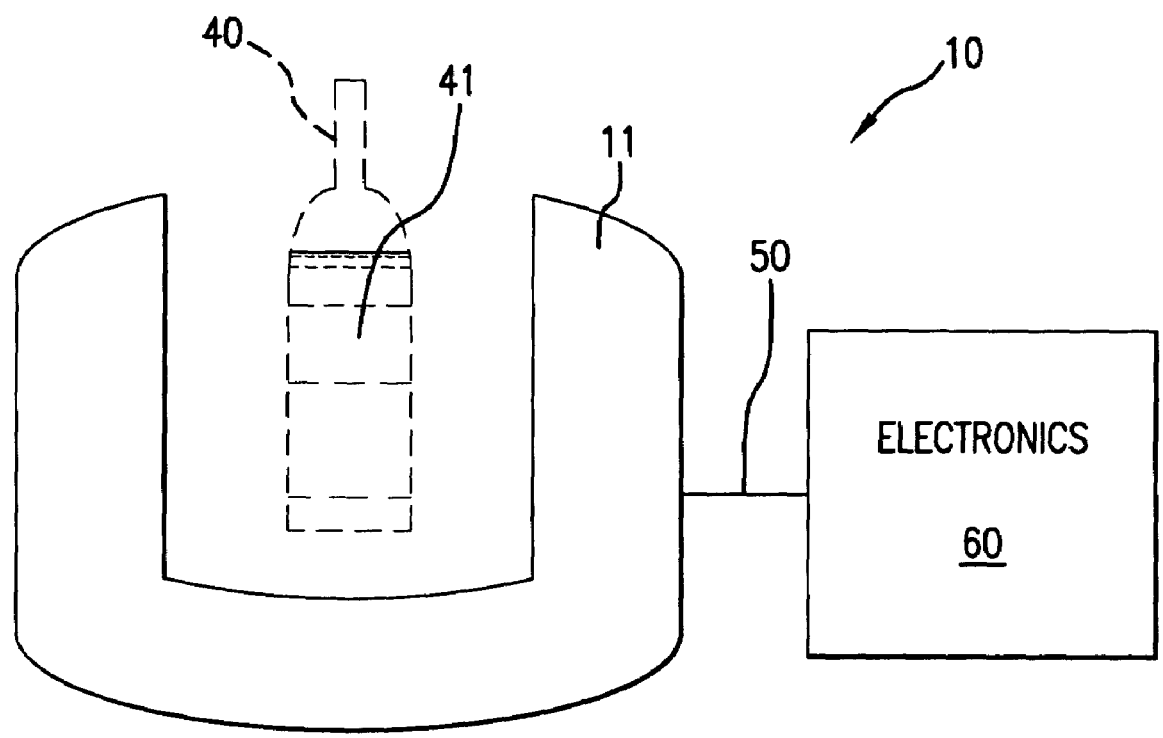
FIG. 1 shows one non-invasive microwave analysis system for liquid containers, in accord with an embodiment.

FIG. 1 shows a non-invasive microwave analysis system 10 for a liquid container 40 (for example, a bottle). Analysis system 10 has a test station 11, electrical connection 50, and electronics 60. Test station 11 is configured to receive liquid container 40, which may contain an unknown liquid 41, as shown.

Analysis system 10 operates by radiating microwaves at liquid container 40, collecting microwaves that scatter from or transmit through liquid container 40 and unknown liquid 41, and analyzing the collected microwaves. The microwaves may, for example, be low energy microwaves.

Analysis system 10 may determine an electrical permittivity and/or an electrical conductivity of liquid container 40 and unknown liquid 41 without opening liquid container 40. Electrical permittivity and/or conductivity are determined by processing scattered amplitude and phase data, and processing the permittivity and conductivity therefrom, as discussed below. While water has high permittivity due to its nature as a polar molecule, many organic molecules (for example, many flammable liquids) have few or no polar components, leading to lower permittivity.

FIG. 2A and FIG. 2B show cross-sectional views of a non-invasive microwave analysis test station 11. Liquid container 40 is not shown in FIG. 2A. A coupling liquid 14 fills a tank 12 to a height 9, forming a top surface 16, as shown. A flexible, non-porous membrane 18 attaches to an upper edge 15 of tank 12 and rests on surface 16 of coupling liquid 14.

Certain details of a transmitter antenna 20 and a receiver antenna 30e are labeled within FIG. 2A. Central conductors (not shown) of each of transmitter antenna 20 and receiver antenna 30e pass through (but are electrically insulated from) tank 12, and connect with electrical connections 50a and 50e respectively. The central conductors of transmitter antenna 20 and receiver antenna 30e are surrounded by cylindrical insulators 21 and 31e, respectively. Outer conductors 22 and 32e shield cylindrical insulators 21 and 31e, and the central conductors, from a bottom surface 13 of tank 12 up to an active transmitting region 24 and an active receiving region 34e, respectively. Cylindrical insulators 21 and 31e and the central conductors are unshielded within active transmitting region 24 and active receiving region 34e.

Transmitter antenna 20 and receiver antenna 30e, and (if existing) other transmitter and receiver antennas, may each take the form of monopole antenna 102' as shown in FIG. 5B of pending U.S. patent application Ser. No. 10/407,886, filed 04 Apr. 2003 and incorporated herein by reference. Active transmitting region 24 and active receiving region 34e (and active transmitting and/or receiving regions of other antennas not visible in this cross-sectional view, see FIG. 3) are typically at the same height with respect to bottom surface 13 of tank 12.

Figure 3:
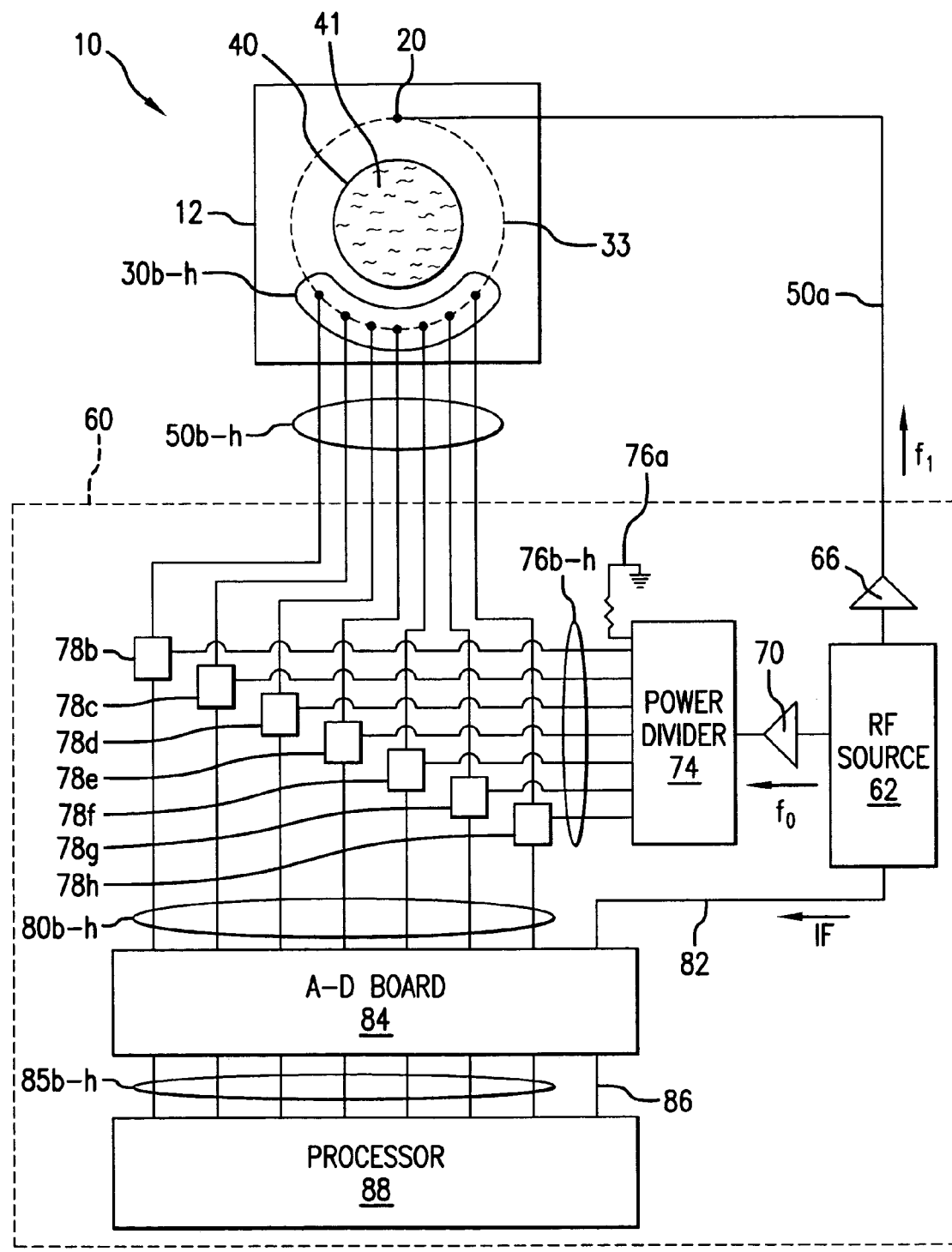
FIG. 3 shows exemplary detail of the non-invasive microwave analysis system of FIG. 1.

To operate test station 11, an operator (not shown) places liquid container 40 on membrane 18 at the center of tank 12, and pushes container 40 downwards to lower it within tank 12. FIG. 2B shows test station 11 with liquid container 40 in place for testing. As shown, coupling liquid 14 compresses membrane 18 around liquid container 40. Coupling liquid 14 (typically a glycerin/water mixture) serves as a coupling medium among transmitter antenna 20, liquid container 40, and receiver antenna 30e (and other receiver antennas, as shown in FIG. 3). Membrane 18 isolates liquid container 40 from coupling liquid 14. Transmitter antenna 20 transmits microwave radiation, which is scattered by liquid container 40 and coupling liquid 14 and received by receiver antenna 30e (and other receiver antennas). Small folds and air gaps (not shown) produced by an imperfect fit of membrane 18 around liquid container 40 have insignificant effect on scattered phase data (discussed below), and/or permittivity and conductivity determined by analysis system 10.

FIG. 3 shows exemplary detail of non-invasive microwave analysis system 10. A top view of tank 12 is shown. Transmitter antenna 20 (connected with electrical connection 50a), liquid container 40 containing unknown liquid 41, and several receiver antennas 30b–30h (each connected with a corresponding electrical connection 50b–50h) are also shown. Receiver antennas 30b–30h may be positioned on the circumference of a circle 33 within tank 12; transmitter antenna 20 also lies on circle 33, as shown.

In the embodiment of FIG. 3, electronics 60 has a radio frequency ("RF") source 62, two amplifiers 66 and 70, an 8-way power divider 74, receiver modules 78b–78h, an 8-channel analog-to-digital ("A–D") board 84, a processor 88, and connections therebetween (the terms "radio frequency" and "RF" as used herein denote association with either of the radio frequency or microwave portions of the electromagnetic spectrum). Electronics 60 may also contain other components (such as, for example, power supplies, data storage devices, displays, and printers), not shown for purposes of illustration. In operation, RF source 62 produces phase locked signals at frequencies $f_0$ and $f_1$, offset by an intermediate frequency reference ("IF"); thus $f_1 = f_0 + IF$. Frequencies $f_0$ and $f_1$ may be, for example, in the range of 500–3000 MHz, and the IF may be, for example, 2 kHz. The $f_1$ signal is amplified by amplifier 66 and fed via electronic connection 50a to transmitter antenna 20. Transmitter antenna 20 transmits microwave radiation of frequency $f_1$ into coupling liquid 14 (e.g., via active transmitting region 24 shown in FIG. 2A and FIG. 2B). The $f_0$ signal from RF source 62 is amplified by amplifier 70 and fed into 8-way power divider 74. 8-way power divider 74 divides the input power from amplifier 70 into outputs 76a–76h. Output 76a terminates, and each output 76b–76h connects with a respective receiver module 78b–78h. Each receiver antenna 30b–30h converts microwave radiation (transmitted by transmitter antenna 20 and scattered by liquid container 40, unknown liquid 41 and coupling liquid 14) into microwave electronic signals, which are sent via one of electrical connections 50b–50h into one of receiver modules 78b–78h, as shown. The steps described below which utilize microwave electronic signals to determine characteristics of unknown liquid 41 within liquid container 40 are collectively denoted herein as "processing," as it should be apparent that processor 88 may perform some of the steps, while others may be performed under the control of processor 88.

Figure 4:
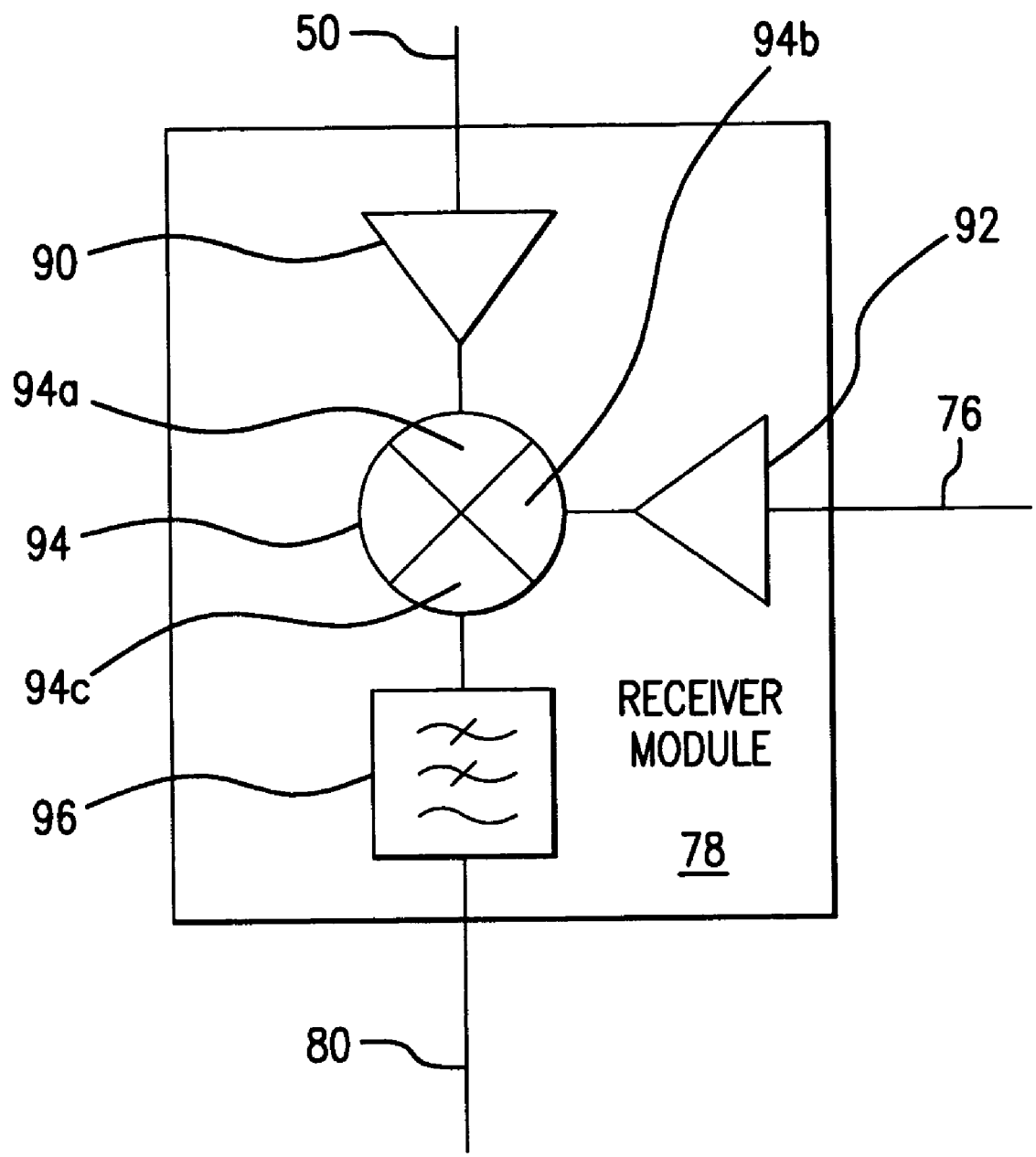
FIG. 4 is a schematic diagram of a receiver module, in accord with an embodiment.

FIG. 4 shows a schematic diagram of one receiver module 78 (e.g., suitable for use as any one of receiver modules 78b–78h of FIG. 3). Electrical connection 50 (e.g., one of electrical connections 50b–50h of FIG. 3) connects with an amplifier 90. Amplifier 90 connects with an RF port 94a of a mixer 94. An output 76 (e.g., one of outputs 76b–76h of FIG. 3) connects with an amplifier 92. Amplifier 92 connects with a local oscillator ("LO") port 94b of mixer 94. An output 94c of mixer 94 connects with a low pass filter 96. The output of low pass filter 96 is thus a down-converted IF signal, which passes into an output 80 (e.g., one of outputs 80b–80h of FIG. 3).

Referring again to FIG. 3, outputs 80b–80h from receiver modules 78b–78h connect with A–D board 84. Line 82 transmits a coherent IF signal from RF source 62 to A–D board 84. A–D board 84 samples the IF signal from line 82 to produce a first digital reference signal, which passes to processor 88 via line 86. Processor 88 uses the first digital reference signal to produce a second digital reference signal 90° out of phase with the first digital reference signal. A–D board 84 also samples the down-converted IF signals in outputs 80b–80h to create corresponding digital signals, which pass to processor 88 via lines 85b–85h. Processor 88 compares the digital signals in lines 85b–85h to the first and second digital reference signals, and processes an amplitude and a phase of the down-converted IF signals in each of outputs 80b–80h. The amplitude and phase data processed by processor 88 are sometimes denoted herein "microwave data."

Processor 88 may also utilize microwave data to process values of permittivity and conductivity, and reconstruct cross-sectional images of the permittivity and conductivity of liquid container 40 within a plane formed by an active transmitting region and active receiving regions (e.g., active transmitting region 24 and active receiving region 34e shown in FIG. 2, and the corresponding active receiving regions of other receiving antennas shown in FIG. 3). Images may be reconstructed using the techniques disclosed in U.S. Pat. No. 6,448,788, issued 10 Sep. 2002 to Meaney et al., and U.S. Pat. No. 5,841,288, issued 24 Nov. 1998 to Meaney et al., both of which are incorporated herein by reference. Processor 88 may also perform other functions such as, for example, controlling operator interface with a test station (e.g., prompting an operator to place or remove a bottle within test station 11), turning components within electronics 60 on and off (e.g., turning RF source 62, A/D board 84 and other components on and off appropriately) and presenting results to the operator. Processor 88 may perform the above-described functions by executing software stored in electronics 60 (e.g., stored in memory devices or other computer-readable media (not shown) of electronics 60). It will be appreciated that processor 88 may be a single unit (e.g., a microprocessor chip) or may be formed from multiple chips, signal processors and/or logic circuits.

The number and arrangement of antennas and associated hardware in a non-invasive microwave analysis system is not limited to the seven-fold circular arrangement of FIG. 3. More receiver antennas provide more detailed data but are costlier to implement, while fewer receiver antennas are cheaper but provide less detailed data. Multiple transmitter antennas may also be located around the periphery of a circle (e.g., circle 33 of FIG. 3) and may be configured to operate sequentially. Antennas may connect with transceivers and/or with an RF switching matrix (such as transceiver array 175 and switch matrix 170 shown in U.S. Pat. No. 6,448,788) so that a given antenna can be used at times as a transmitter antenna, and at other times as a receiver antenna. Transmitter and receiver antennas may be arranged in non-circular arrangements.

Figure 5:
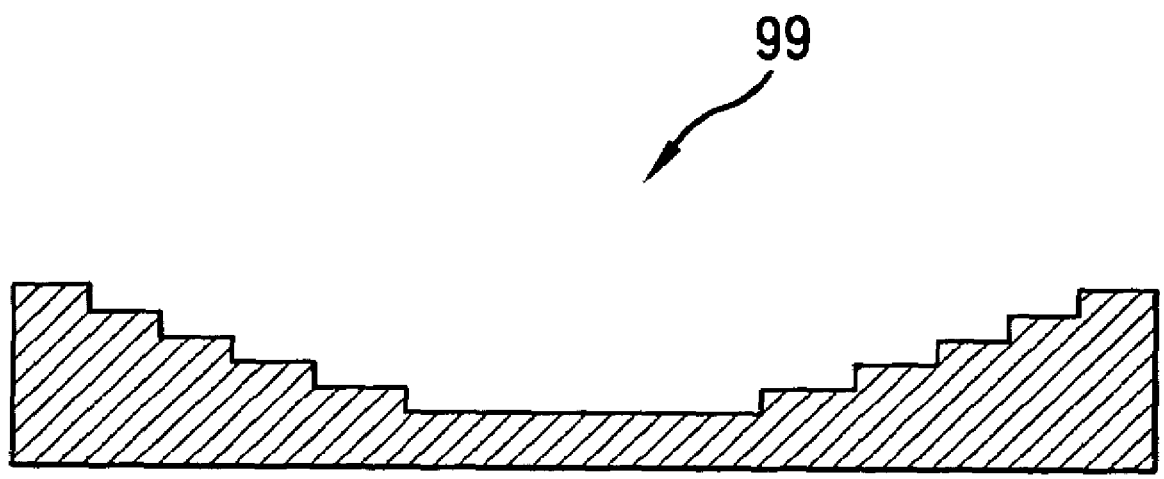
FIG. 5 is a cross-sectional view of a base with concentric circular indentations, in accord with an embodiment.

In order to take advantage of the cylindrical symmetry of most liquid containers (i.e., round bottles or jars) for data manipulation purposes, a container to be tested is typically centered within the transmitter antenna and receiver antenna arrangement (e.g., liquid container 40 is centered within circle 33 of FIG. 3). FIG. 5 is a cross-sectional view of a base 99 with concentric circular indentations, for use as a centering jig (e.g., in tank 12 of test station 11). Visual and tactile cues provided by base 99 enable an operator to center liquid container 40 easily and quickly within test station 11.

Figure 6A:
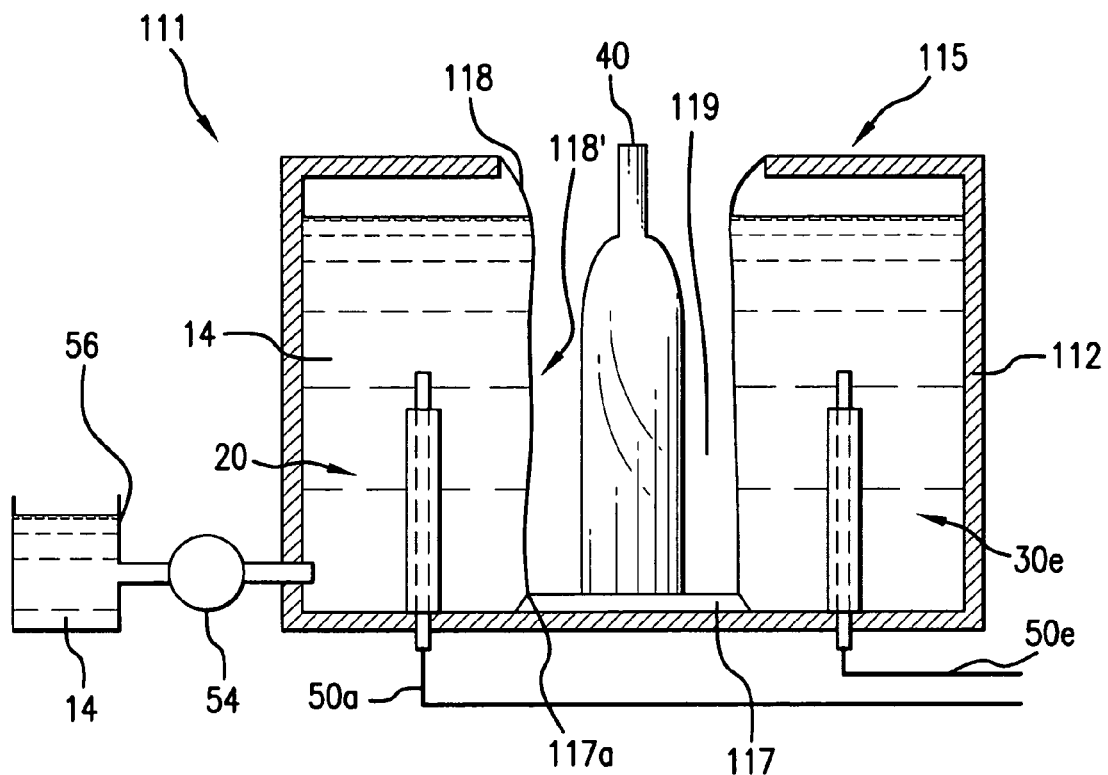
FIG. 6A and FIG. 6B are cross-sectional views of another non-invasive microwave analysis test station, in accord with an embodiment, and a liquid container.
Figure 6B:
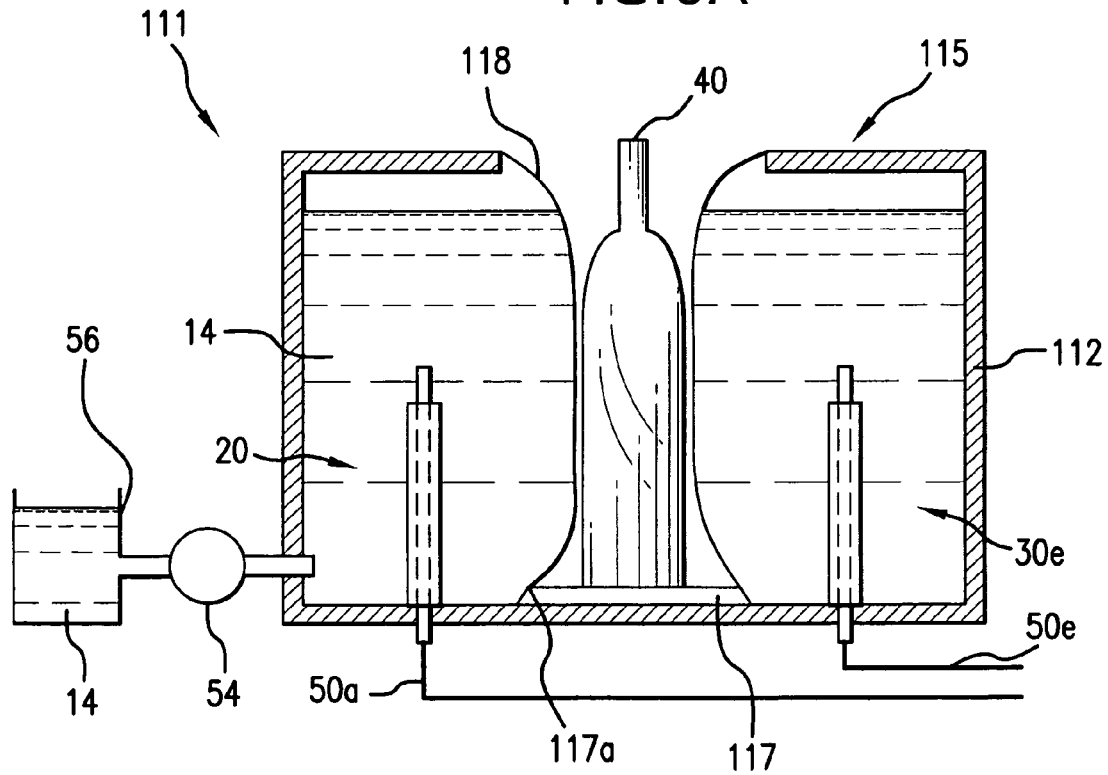

The membrane that separates the coupling liquid from the liquid container may extend at least partially beneath a surface of the coupling liquid, without a liquid container in place. FIG. 6A and FIG. 6B show cross-sectional views of another non-invasive microwave analysis test station 111 and a liquid container 40. A tank 112 of test station 111 has a rigid top surface 115. A base 117 is within tank 112. A membrane 118 attaches both to top surface 115 and to a top corner 117a of base 117, sealing off coupling liquid 14 within tank 112 from a space 119 above base 117. A fluid reservoir 56 contains coupling liquid 14; reservoir 56 connects with tank 112 through a pump 54, as shown. Other parts of test station 111 are, for example, identical to the corresponding parts of test station 11, shown in FIG. 2A and FIG. 2B.

To operate test station 111, an operator first places liquid container 40 on base 117. FIG. 6A shows test station 111 in a "standby" state (i.e., during exchange of liquid containers between tests), with liquid container 40 resting on base 117. In the standby state, the elasticity of membrane 118, and its attachment around top corner 117a of base 117, may hold membrane 118 in an open position; that is, membrane 118 forms a substantially vertical wall 118' that separates coupling liquid 14 from open space 119 above base 117. Pump 54 may also pump a quantity of coupling liquid 14 from tank 112 into reservoir 56, decreasing pressure within tank 112 to help hold membrane 118 in the open position. During testing of liquid container 40, pump 54 pumps additional coupling liquid 14, under pressure, into tank 112. The increased pressure within tank 112 causes membrane 118 to expand towards, and make contact with, liquid container 40. An operator may visually monitor the expansion of membrane 118 to ensure adequate contact of membrane 118 around liquid container 40. Pump 56 may be controlled by a manual switch or foot pedal (not shown), or by a processor (not shown) executing software stored in computer-readable media, for example.

FIG. 6B shows test station 111 in a "testing" state, with liquid container 40 resting on base 117 and in circumferential contact with membrane 118. Test station 111 performs microwave testing (such as described above) while in the testing state. When testing is complete, pump 54 pumps some of coupling liquid 14 from tank 112 into reservoir 56 so that test station 111 re-enters the standby state, and membrane 118 releases its position for easy removal of liquid container 40. As discussed above with respect to test station 11, a processor (not shown) may control operator interface to test station 111 by executing software stored in computer-readable media, for example.

Other configurations exist to isolate a coupling liquid from a liquid container. For example, instead of a flexible membrane being attached around a base (as in FIG. 6A and FIG. 6B), the membrane may form a sac which attaches to a wall of a tank. The membrane sac may hang down into coupling liquid, and the bottom of the sac may or may not touch the tank. A membrane sac may also include structure which holds it in an open state (i.e., for exchanging liquid containers easily) but which collapses under external pressure (i.e., for testing).

Figure 7A:
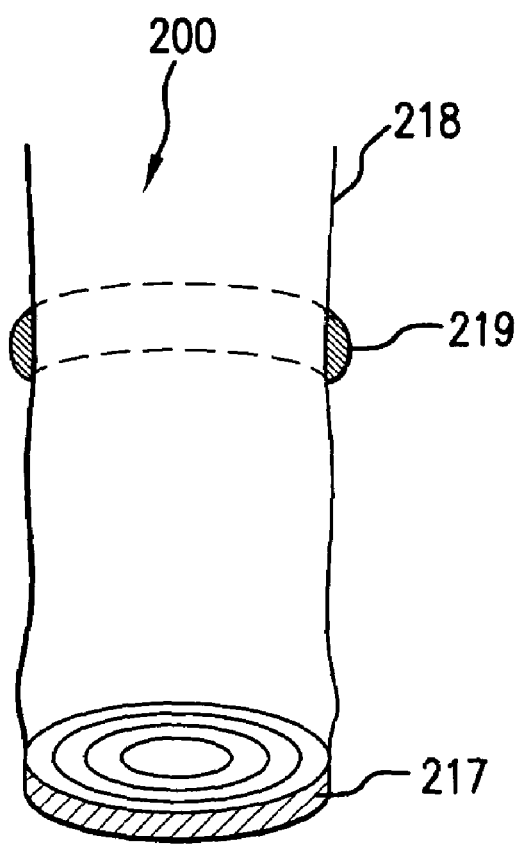
FIG. 7A and FIG. 7B are cutaway views of a membrane sac, in accord with an embodiment.
Figure 7B:
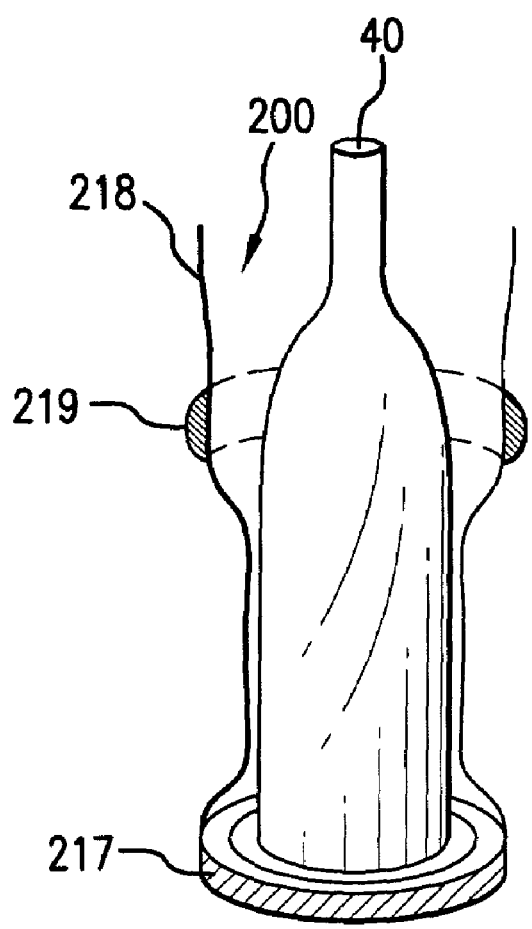

FIG. 7A shows a cutaway view of one such membrane sac 200 in an open state. A rib member 219 is shown in cutaway cross-section; dashed lines indicate the continuation of rib member 219 behind a rear portion of a membrane 218. FIG. 7A also shows a base member 217. FIG. 7B is a cutaway view of membrane sac 200 under external pressure with liquid container 40 in place. Rib member 219 and base member 217 hold part of membrane 218 in its approximate original shape, while other parts of membrane 218 collapse around liquid container 40.

Sac 200 may be constructed, for example, as a double walled sac that a coupling liquid may inflate to surround a liquid container. Interchangeable test station fixtures may enable easy and rapid exchange of membrane sacs adapted to liquid containers of various sizes.

Figure 8A:
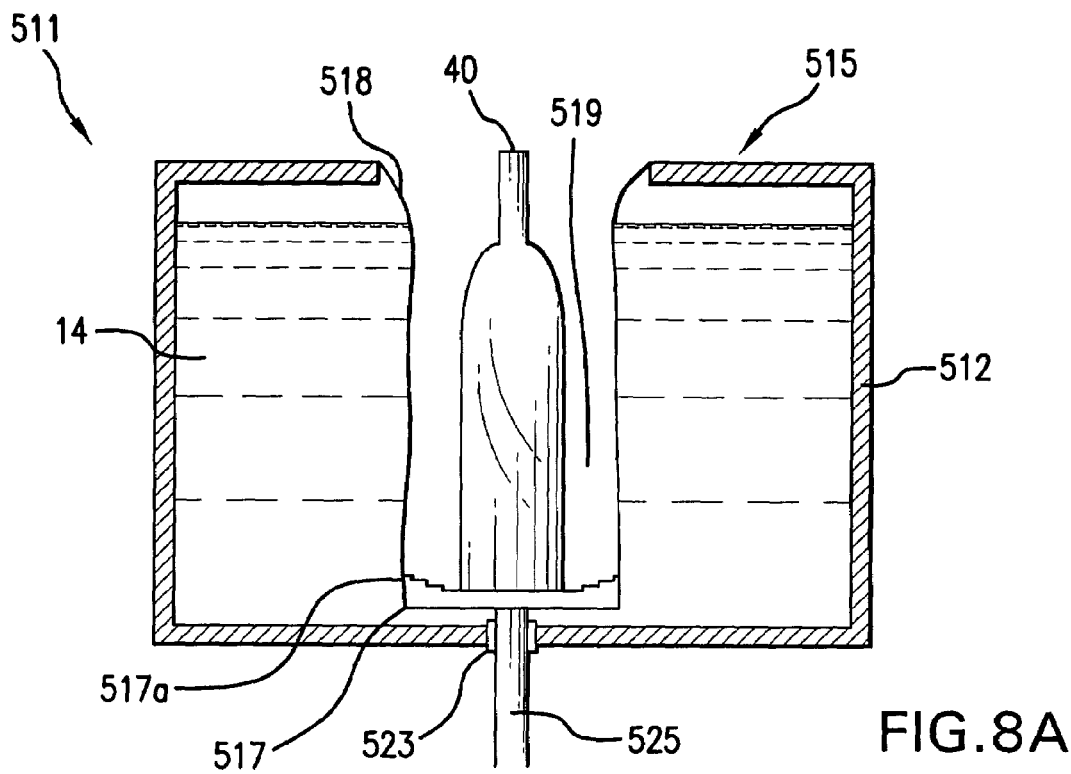
FIG. 8A and FIG. 8B are cross-sectional views of another non-invasive microwave analysis test station, in accord with an embodiment, and a liquid container.
Figure 8B:
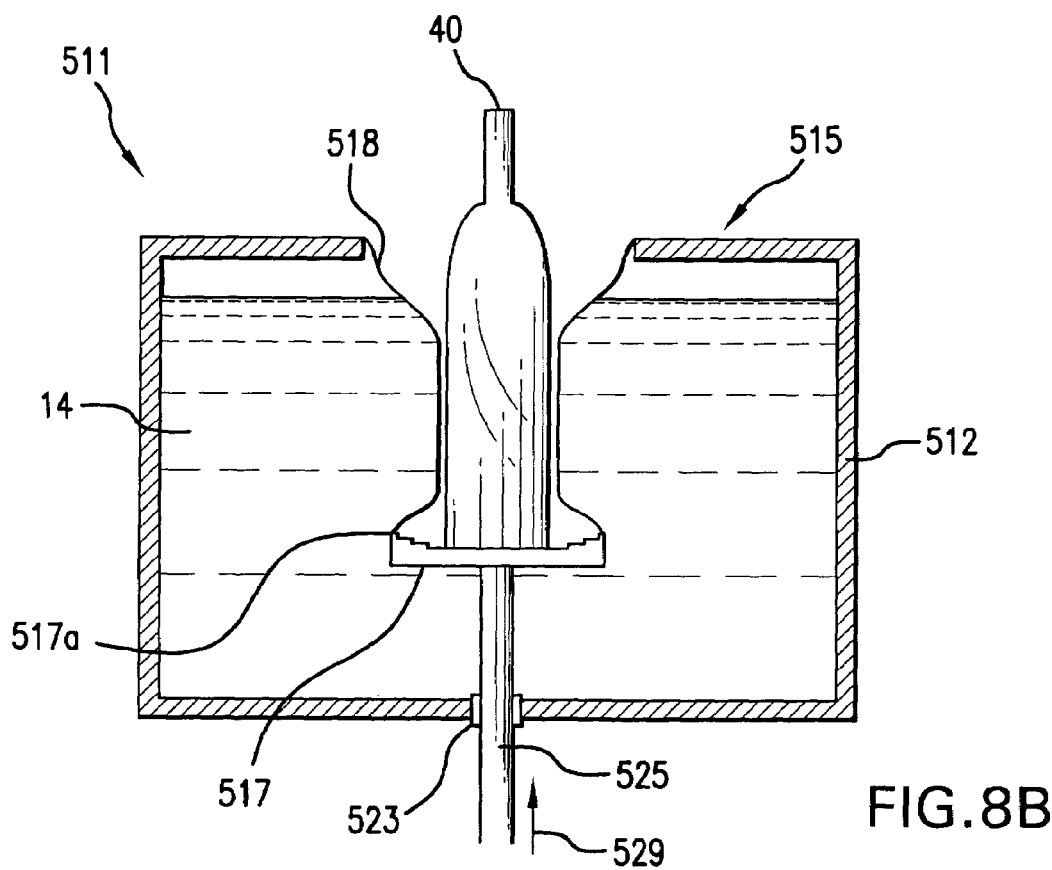

FIG. 8A and FIG. 8B show cross-sectional views of another non-invasive microwave analysis test station 511 and a liquid container 40. In FIG. 8A, a base 517 connects with a rod 525 that passes through a hydraulic seal 523 in a tank 512, as shown. A membrane 518 attaches to a top corner 517a of base 517, and a top surface 515 of tank 512, as shown. Tension in membrane 518 holds back coupling liquid 14 throughout a space 519, so that the area above base 517 is clear, as shown. FIG. 8A therefore shows test station 511 in a "standby" state for exchange of liquid containers.

On the other hand, FIG. 8B shows test station 511 in a "testing" state. In FIG. 8B, rod 525 has been pushed upwards (i.e., in the direction of arrow 529), raising base 517 and liquid container 40 relative to the positions shown in FIG. 8A. When base 517 raises, the tension within membrane 518 releases, and membrane 518 collapses against liquid container 40 under the pressure of coupling liquid 14. As discussed above with respect to test stations 11 and 111, a processor (not shown) may control operator interface to test station 511 (for example, controlling the motion of rod 525) by executing software stored in computer-readable media, for example.

Figure 9:
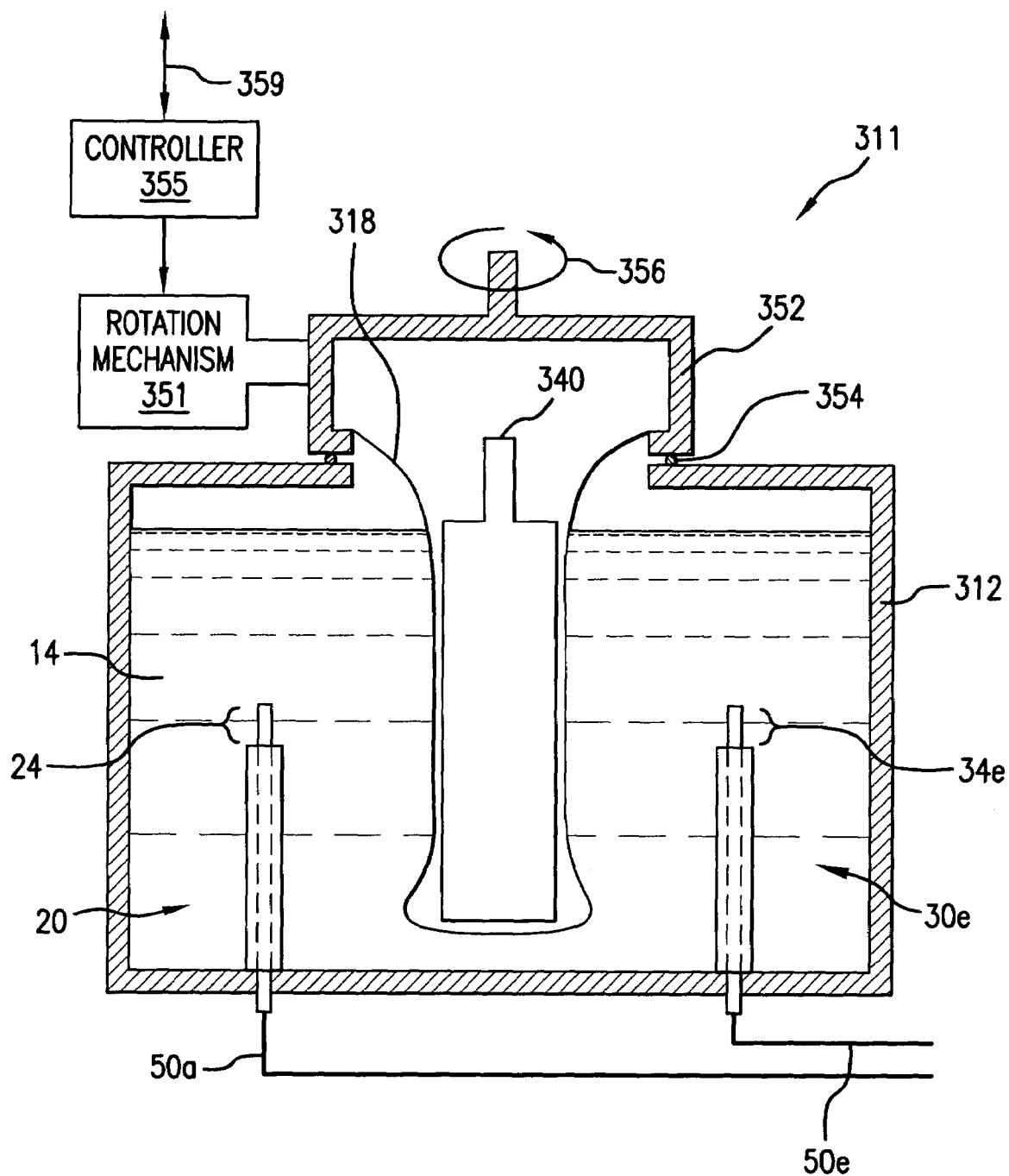
FIG. 9 is a cross-sectional view of a non-invasive microwave analysis test station that is configured for testing of an asymmetric liquid container, in accord with an embodiment.

Asymmetric liquid containers may be tested using test station fixtures that rotate a liquid container (and, optionally, a membrane). FIG. 9 shows a non-invasive microwave analysis test station 311 configured to test an asymmetric liquid container 340. A tank 312 holds coupling liquid 14. A rotating fixture 352 mates with tank 312 at a seal 354. A flexible, non-porous membrane 318 attaches to rotating fixture 352. A liquid container 340 is positioned within membrane 318, as shown. Other parts of test station 311 are for example identical to the corresponding parts of test station 11 as shown in FIG. 2A and FIG. 2B.

During testing, a rotation mechanism 351 rotates rotating fixture 352, membrane 318, and liquid container 340, as shown by arrow 356. A controller 355 controls the rotational angle of rotating fixture 352, and sends rotational angle data to electronics (not shown) through interface 359. Microwave radiation is transmitted and received within tank 312, and is converted to microwave data as discussed with respect to FIG. 3, with rotating fixture 352 and liquid container 340 at multiple angles of rotation within test station 311.

A processor (not shown) of test station 311 associates the angle of rotation with microwave data taken at each angle of rotation, and creates a data structure used to reconstruct an image of liquid container 340 in a plane formed by active transmitting and receiving regions 24 and 34e (and other receiving regions, not shown). The image reconstruction techniques discussed with respect to FIG. 3 apply, except that symmetry of liquid container 340 is not assumed. Rotating fixture 352 may rotate in a stepwise or continuous fashion while microwave data is taken, and may rotate liquid container 340 through a partial or a complete rotation. For example, the use of multiple transmitter antennas, or switching certain antennas from transmitter antennas to receiver antennas, or vice versa, as discussed with respect to FIG. 3, may enable reduction in the number of physical angles through which liquid container 340 rotates to create a data structure sufficient for reconstruction of a two-dimensional image. Taking microwave data at fewer angles is faster but results in a less detailed image; taking data at more angles takes longer but provides more detail. As discussed above with respect to test stations 11, 111 and 511, a processor (not shown) may control operator interface to test station 311 (e.g., controlling access to container 340 and rotation of fixture 352) by executing software stored in computer-readable media, for example.

In certain embodiments, rotating fixture 352 may be open (or be configured to open easily) to allow easy insertion and removal of liquid containers. The interface between a tank and a rotating fixture may or may not be a seal. Transmitter and receiver antennas may mount on a rotatable structure and rotate about a fixed liquid container, instead of the liquid container rotating within fixed antennas.

Figure 10:
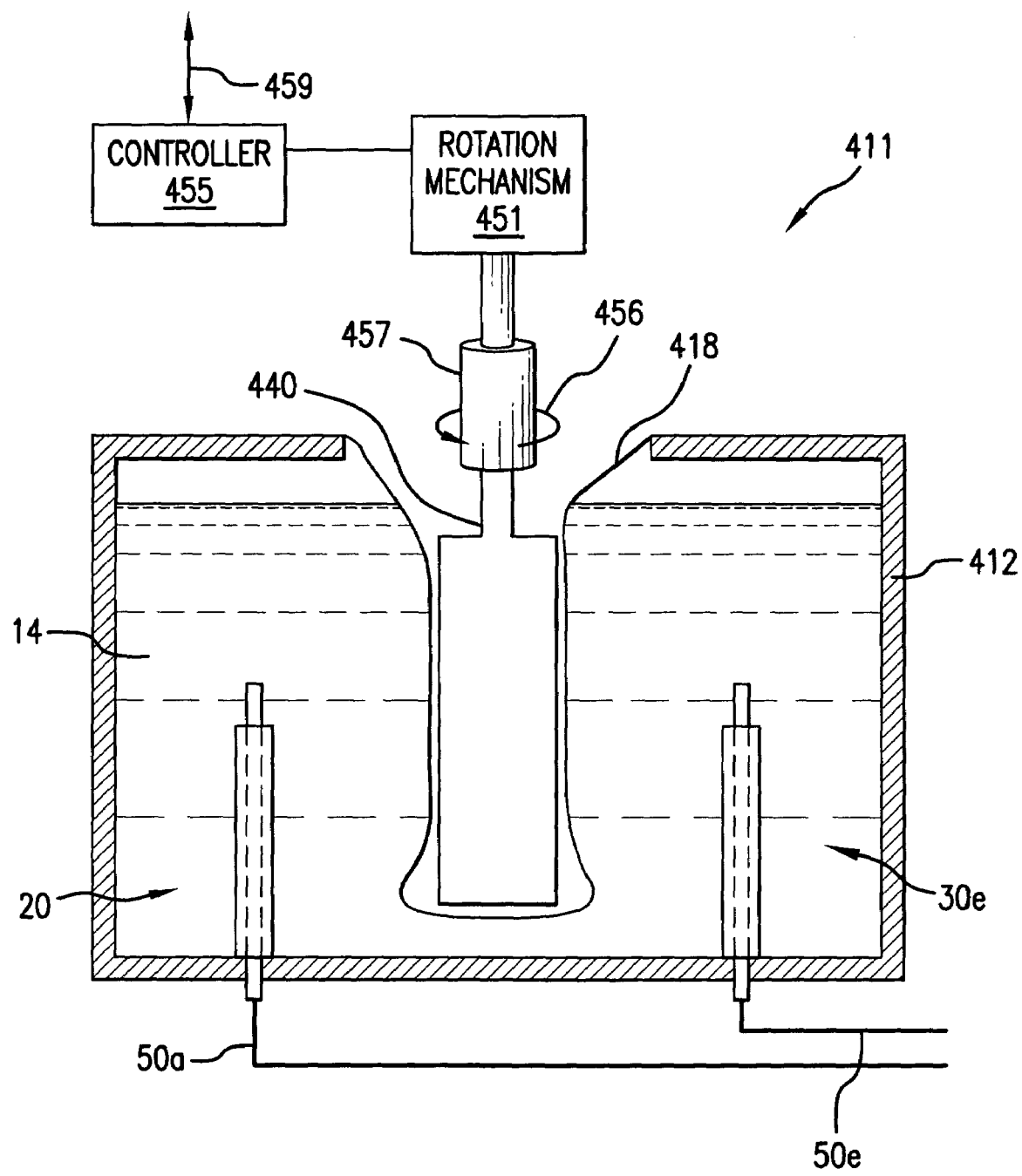
FIG. 10 is a cross-sectional view of another non-invasive microwave analysis test station that is configured for testing of an asymmetric liquid container, in accord with an embodiment.

A non-invasive microwave analysis test station may have a clamping mechanism adapted to grip the liquid container directly, rather than via a rotating fixture that rotates a membrane with a liquid container. FIG. 10 shows a non-invasive microwave analysis test station 411 configured for testing of an asymmetric liquid container 440. A clamp 457 holds liquid container 440, to rotate it within a tank 412 in the direction shown by arrow 456. A controller 455 connects with a processor (not shown) through interface 459, and sends rotational angle data, which is associated with microwave data in the manner discussed with respect to FIG. 9. A non-porous, flexible membrane 418 surrounds liquid container 440. Membrane 418 may either slip as liquid container 440 rotates within it, or may have sufficient proportions and elasticity so as to cling to, and wrap around, liquid container 440 as it rotates. Other parts of test station 411 are for example identical to the corresponding parts of test station 11 as shown in FIG. 2A and FIG. 2B. As discussed above with respect to test stations 11, 111, 511 and 311, a processor (not shown) may control operator interface to test station 411 by executing software stored in computer-readable media, for example.

In one embodiment, a non-invasive microwave analysis system acquires microwave data for a reference container, and stores the microwave data as calibration data. When the analysis system thereafter acquires new microwave data for a liquid container with unknown contents ("unknown container"), the calibration data may be subtracted from the new microwave data, resulting in "scattered field data" (for example, including "scattered amplitude data" and "scattered phase data" for each transmitter antenna/receiver antenna combination of the analysis system). Reference containers may be of various sizes and shapes, enabling selection of appropriate calibration data for subtraction from microwave data of a similarly sized and shaped unknown container. Reference containers may optionally contain a reference liquid (e.g., water, or coupling liquid, such as coupling liquid 14) when the calibration data is taken. Calibration data may also be taken on empty reference containers for comparison to empty unknown containers.

Figure 11:
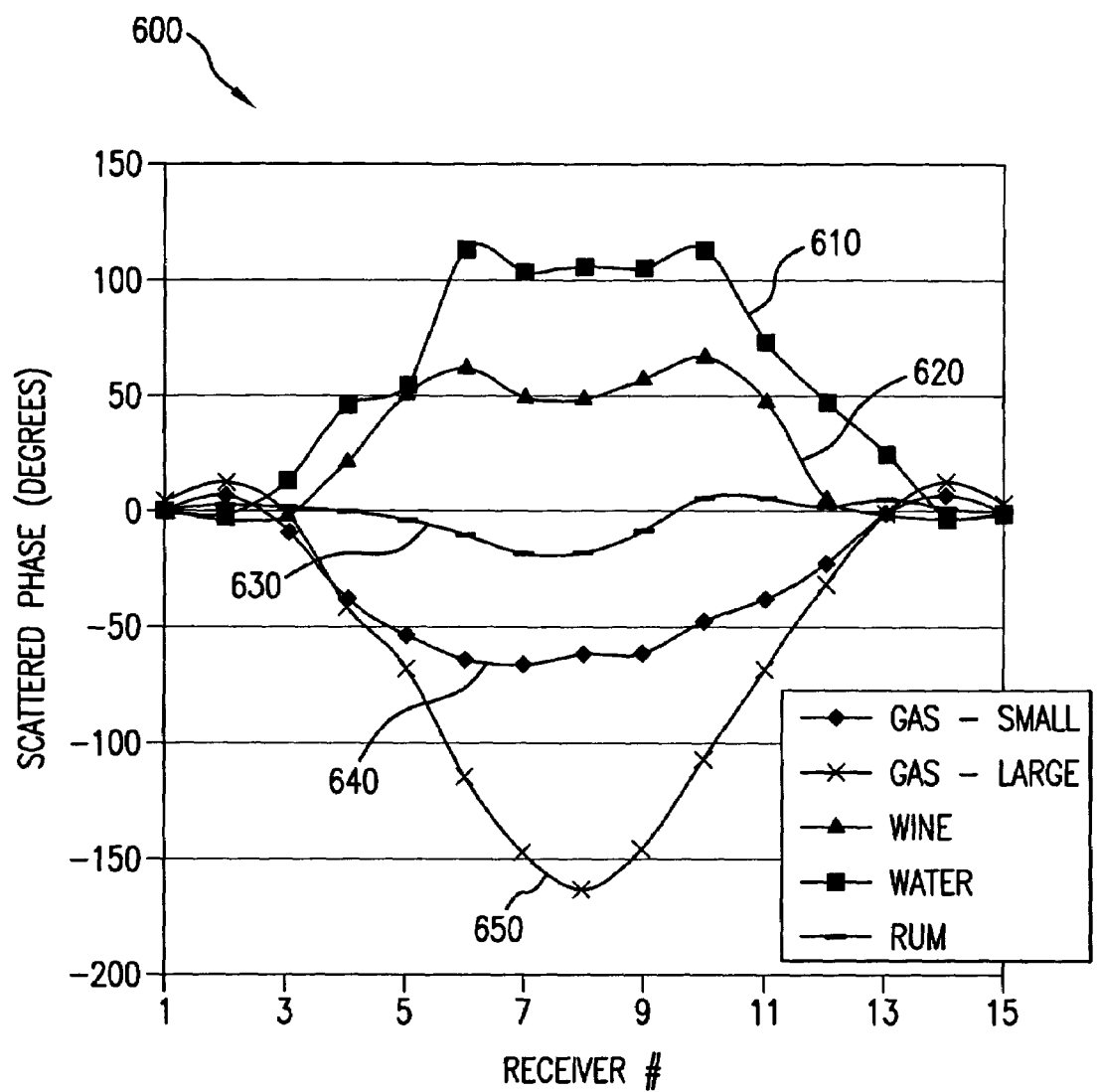
FIG. 11 is a graph of data from testing of containers of various liquids.

A non-invasive microwave analysis system may use scattered phase data alone to discriminate between benign and hazardous liquids, without reconstructing images. FIG. 11 is a graph 600 of data from testing of containers of various liquids. The system that generated the data of FIG. 11 had liquid directly in contact with the containers. Curves 610, 620, 630, 640 and 650 show scattered phase data collected from tests of containers containing water, wine and rum, and two containers of gasoline, respectively. It may be seen that when more polar liquids are present (e.g., water and wine, forming curves 610 and 620), scattered phase data is different from the scattered phase data when less polar liquids are present (e.g., 151 proof rum and two gasoline containers, forming curves 630, 640 and 650). Also, containers that present air within the plane of the transmitter and receiver antennas (e.g., containers that are partially or completely empty) may have phase shifts and permittivity similar to those associated with less polar molecules, since the permittivity of air is about equal to 1.

Therefore, liquid containers may be screened, for example, by scattered phase data alone. Illustratively, a non-invasive microwave analysis system may prompt an operator to enter the liquid expected to be in a container (e.g., by asking a passenger what is in the container and then entering the passenger's answer). A look-up table utilizes the expected liquid information to generate a failure threshold for a measured phase value of the container. Referring to FIG. 11, a failure threshold assigned to "water" may be +50 degrees, a failure threshold assigned to "wine" may be 0 degrees, and a failure threshold assigned to "hard liquor" may be −50 degrees. The analysis system then compares the scattered phase data with the failure threshold, and reports the result to the operator as a simple "pass" or "fail." A result of "fail" may alert the operator to perform more thorough testing (e.g., to have the analysis system gather and/or process data to provide full permittivity and conductivity images), or to inspect contents of the container directly.

Conductive liquids and/or conductive containers may present challenges to the non-invasive microwave analysis system described herein, because microwaves do not penetrate conductive materials. However, image reconstruction (as described in the patents incorporated herein by reference) allows display of any part of a container and/or its contents which is conductive; thus, conductivity images may be used to alert authorities to inspect contents of certain unknown containers in a direct manner—for example, containers whose contents cannot be imaged (e.g., metallic containers) or which present suspicious images (e.g., a conductivity image of an object hidden within a bottle).

In addition to analyzing or imaging containers of liquids, non-invasive microwave analysis systems may be used for analyzing or imaging biological subjects. For example, it may be desirable to use a non-invasive analysis system to image a biological subject when direct contact between the subject and a coupling liquid is undesirable (e.g., when imaging a head of a live biological subject, raising a concern about drowning).

Figure 12A:
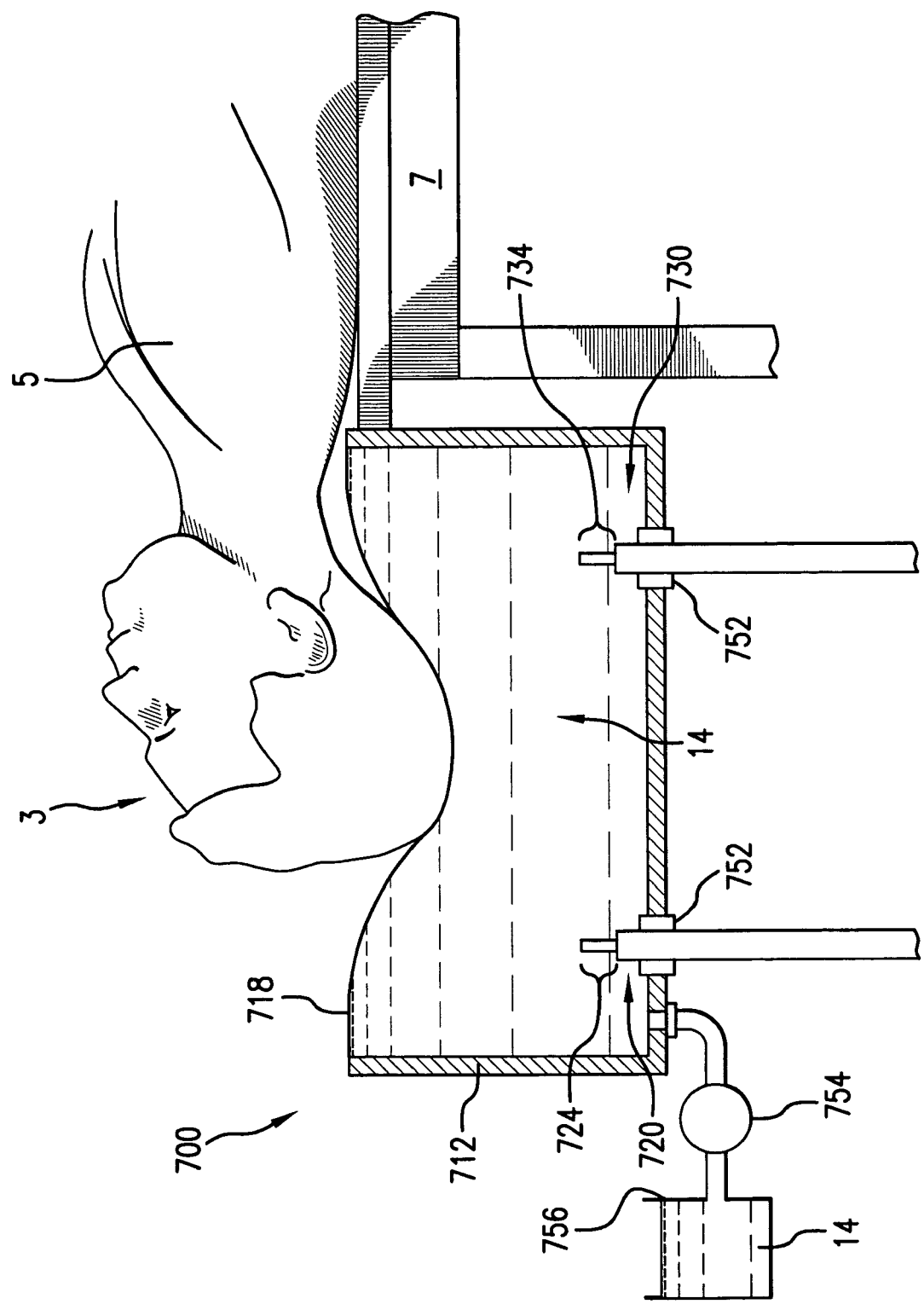
FIG. 12A is a schematic diagram of a non-invasive microwave analysis test station that images a biological subject, in accord with an embodiment.

FIG. 12A is a schematic diagram of a non-invasive microwave analysis test station 700 for imaging a portion 3 (e.g., a head) of a biological subject 5 (e.g., a human). A tank 712 holds coupling liquid 14 that is bounded by a membrane 718. A transmitting antenna 720 and receiving antennas 730 mount within tank 712 utilizing hydraulic seals 752 (only one of receiving antennas 730 is shown, for clarity of illustration). Transmitting antenna 720 and receiving antennas 730 connect with electronics for generating, receiving and analyzing microwave signals (e.g., like electronics 60 of non-invasive microwave analysis system 10 discussed above). A fluid reservoir 756 contains coupling liquid 14; reservoir 756 connects with tank 712 through a pump 754. Pumping some of coupling liquid 14 from tank 712 to reservoir 756 puts test station 700 in a "standby" state. Antennas 720, 730 and other receiving antennas may be in a lowered position (e.g., lowered through hydraulic seals 752) in the standby state.

Figure 12B:
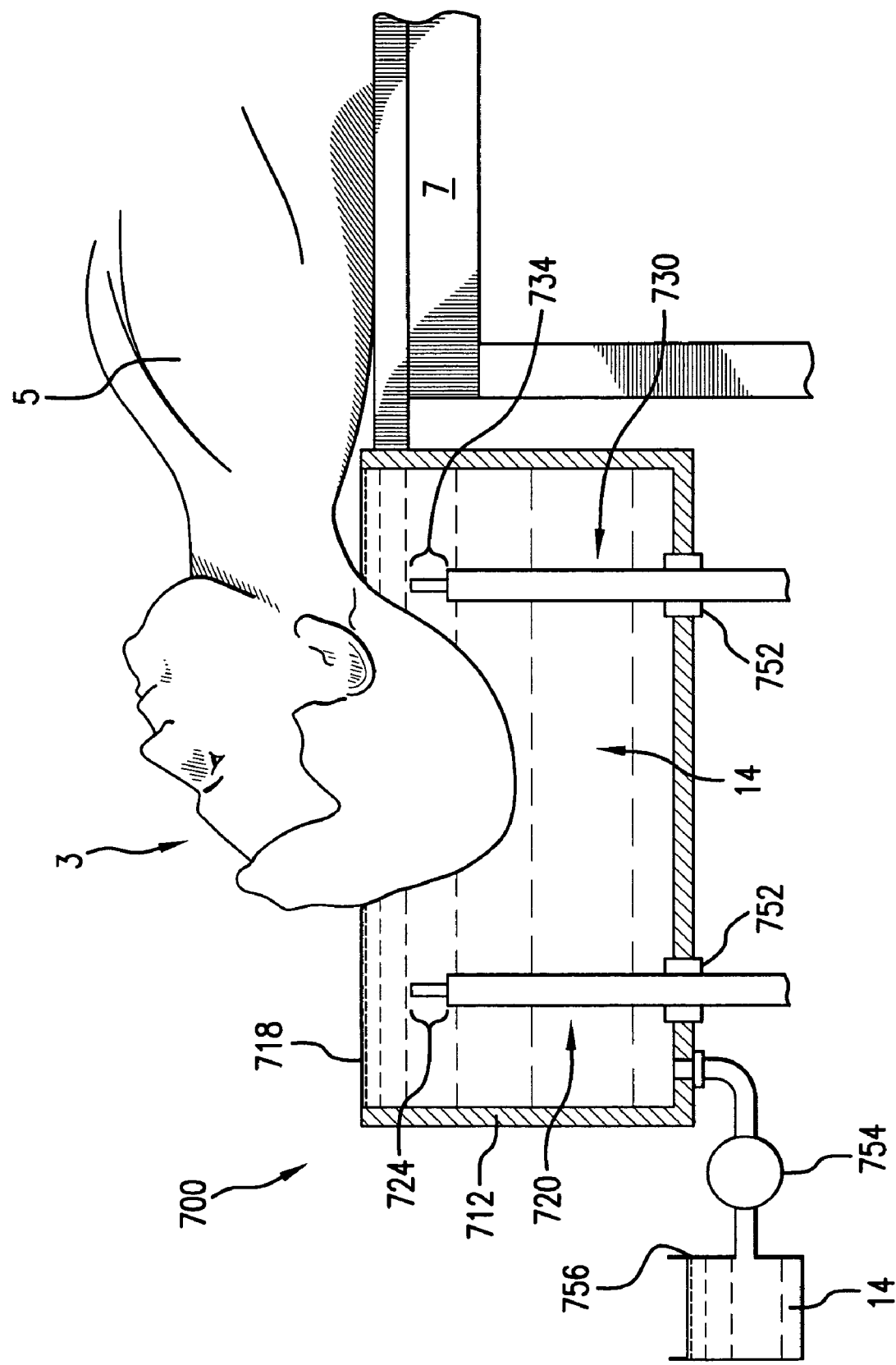
FIG. 12B shows the test station and subject of FIG. 12A during imaging

Illustratively, imaging using test station 700 begins with biological subject 5 on a table 7, with portion 3 extending over tank 712 in the "standby" state, as shown. Pump 754 pumps coupling liquid 14 into tank 712, under pressure, so that liquid 14 compresses membrane 718 around portion 3. FIG. 12B shows test station 700 and subject 5 during imaging. With liquid 14 substantially surrounding portion 3 (but separated from portion 3 by membrane 718), microwaves are transmitted, received and analyzed in the same manner as described above. The steps which utilize microwave electronic signals to determine characteristics of portion 3, including image reconstruction, are collectively denoted herein as "processing," as it should be apparent that some of the steps will be performed by a processor, while others may be performed under the control of a processor, for example.

Raising antennas 720 and 730 (and receiver antennas not shown in FIG. 12B) through hydraulic seals 752 moves a plane formed by an active transmitting region 724 of transmitter antenna 720 and active receiving region 734 of receiver antenna 730 (and active receiving regions of other receiver antennas); this movement allows capture of data that may be processed to reconstruct images of various planes within portion 3. As discussed above with respect to FIG. 3, antennas may connect with transceivers and/or with an RF switching matrix, so that a given antenna can be used at times as a transmitter antenna, and at other times as a receiver antenna, to allow capture of data from various illumination angles. As discussed above with respect to test stations 11, 111, 511, 311 and 411, a processor (not shown) may control operator interface to test station 711 by executing software stored in computer-readable media, for example.

Figure 13:
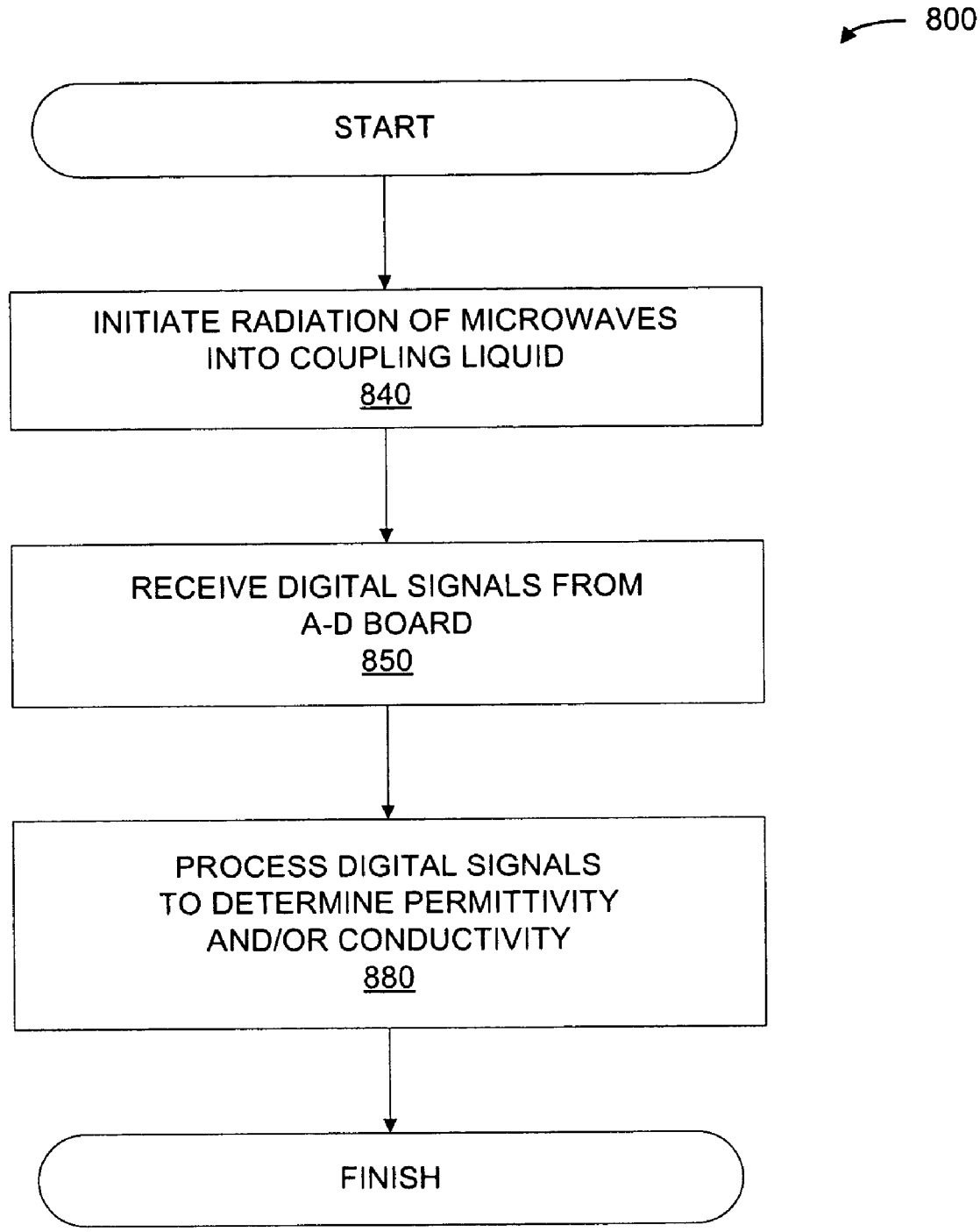
FIG. 13 is a flowchart of one non-invasive microwave analysis process, in accord with an embodiment.

FIG. 13 is a flowchart of one non-invasive microwave analysis process 800. Process 800 may be performed, for example, by a processor of a non-invasive microwave analysis system (e.g., by processor 88 (FIG. 3) of non-invasive microwave analysis system 10 (FIG. 1)) to determine permittivity and/or conductivity of an unknown liquid (e.g., liquid 41). Step 840 controls the transmission of microwave radiation (e.g., controls power and/or connections of RF source 62 to generate a signal that a transmitter antenna 20 or 720 transmits as microwave radiation) into coupling liquid of the analysis system. Step 850 receives digital signals corresponding to down-converted IF signals from an A–D board, corresponding to: (a) antennas 30 or 730 converting scattered microwave radiation to microwave electronic signals, (b) receiver modules 78 processing the microwave electronic signals into down-converted IF signals, and (c) A–D board 84 digitizing the down-converted IF signals, as shown in FIG. 3. Step 880 processes the digital signals to determine permittivity and/or conductivity of the unknown liquid.

Figure 14:
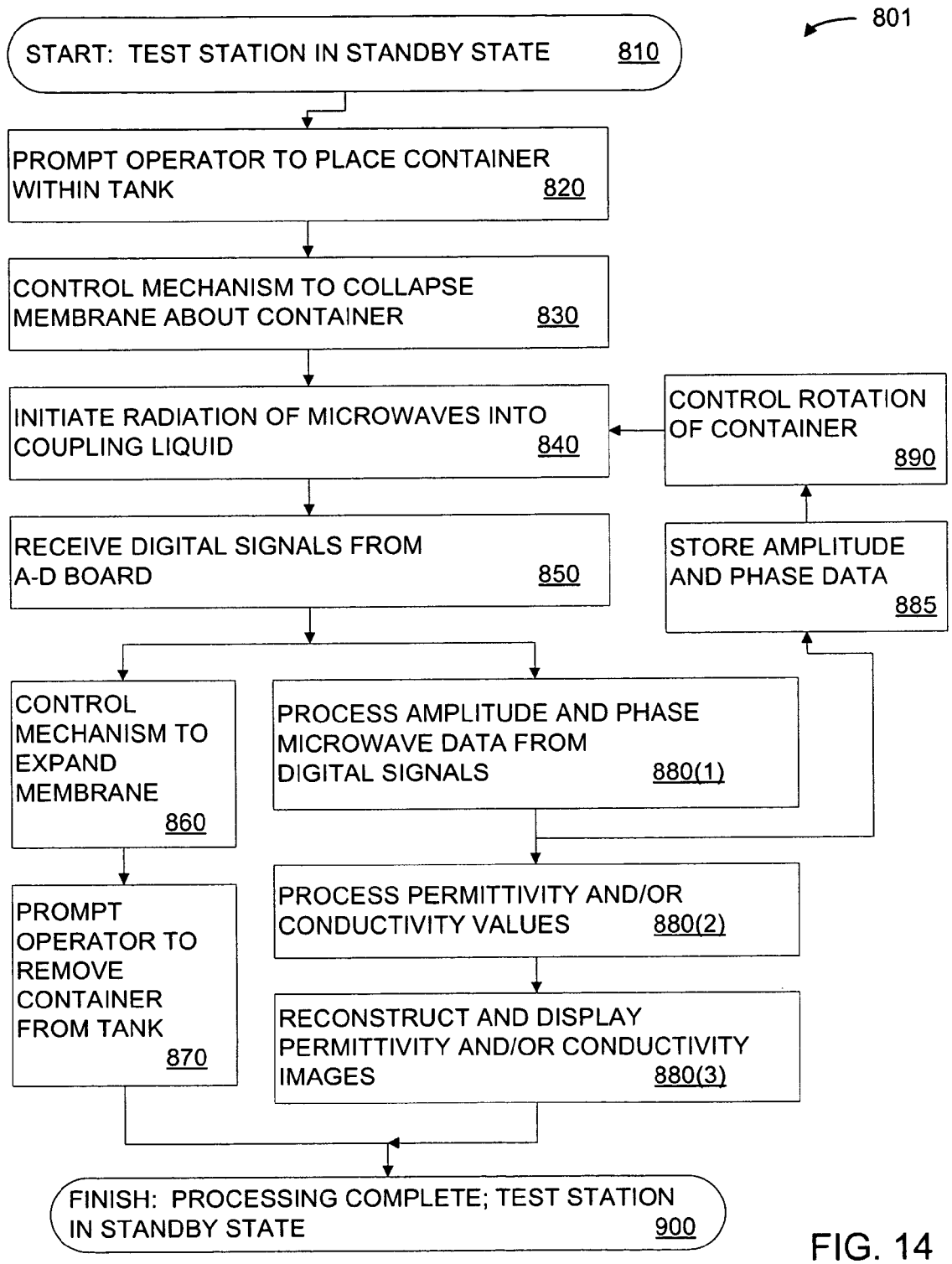
FIG. 14 is a flowchart of another non-invasive microwave analysis process, in accord with an embodiment.

FIG. 14 is a flowchart of one non-invasive microwave analysis process 801. Process 801 may be performed, for example, by a processor of a non-invasive microwave analysis system (e.g., by processor 88 (FIG. 3) of non-invasive microwave analysis system 10 (FIG. 1)) to determine permittivity and/or conductivity of an unknown liquid (e.g., liquid 41). In step 810, a test station is in a standby state so that a tank of the test station (e.g., any of tanks 12, 112, 512, 312 or 412) is available to accept a container for analysis. Step 820 prompts an operator to place the container within the tank. Step 830 controls a mechanism that collapses a membrane that separates the container from the coupling liquid about the container so that testing may proceed (e.g., processor 88 controls a pump 54 that pressurizes coupling liquid 14, see FIG. 6A and FIG. 6B, or processor 88 controls a motor that manipulates a base 517 on which the container rests, see FIG. 8A and FIG. 8B). Step 840 controls transmission of microwave radiation (e.g., controls power and/or connections of RF source 62 to generate a signal that a transmitter antenna 20 or 720 transmits as microwave radiation) into the coupling liquid. Step 850 receives digital signals corresponding to down-converted IF signals from an A–D board, corresponding to: (a) antennas 30 or 730 converting scattered microwave radiation to microwave electronic signals, (b) receiver modules 78 processing the microwave electronic signals into down-converted IF signals, and (c) A–D board 84 digitizing the down-converted IF signals, as shown in FIG. 3. Step 860 controls a mechanism to expand the membrane to facilitate removal of the container (e.g., processor 88 controls a pump 54 that depressurizes coupling liquid 14, see FIG. 6A and FIG. 6B, or processor 88 controls a motor that manipulates a base 517 on which the container rests, see FIG. 8A and FIG. 8B). Step 870 prompts the operator to remove the container from the test station. After step 870, the test station is again in the standby state. As suggested by the branched arrow from step 850 to both of steps 860 and 880(1), the sequences of (a) steps 860 and 870, and (b) steps 880(1)–880(3) may be performed in either order (e.g., steps 860 and 870 may be completed first to allow a sample to be physically removed from the test station while processing steps 880(1)–880(3) occur). Step 880(1) processes amplitude and phase microwave data from the digital signals. Amplitude and phase data may be stored in step 885, and step 890 controls rotation of the container if multiple angles of rotation are desired for analysis of asymmetric containers (e.g., see FIG. 9 and FIG. 10). Step 880(2) processes permittivity and/or conductivity values, and step 880(3) reconstructs permittivity and/or conductivity images; when multiple angles of rotation are used, steps 880(2) and 890(2) may include associating rotation angle data with the microwave data. Process 801 terminates in step 900 with processing complete and with the test station in the standby state.

The steps listed in processes 800 and 801 are intended to be exemplary; it will be appreciated that certain steps of processes 800 and 801 may be performed differently, performed in a different order, or omitted without departing from the scope and spirit hereof. For example, as discussed above, when a liquid container is symmetric, multiple angles of rotation may not be required, so steps 885 and 890 may be omitted. Containers may be screened based on phase data alone, in which case steps 880(2) and 880(3) may be omitted. In certain test stations, the step of inserting the container into the test station may collapse a membrane separating the container from the coupling liquid by pushing the container downwards on the membrane (see for example the test station of FIG. 2A and FIG. 2B), so step 820 includes step 830.

Figure 15:
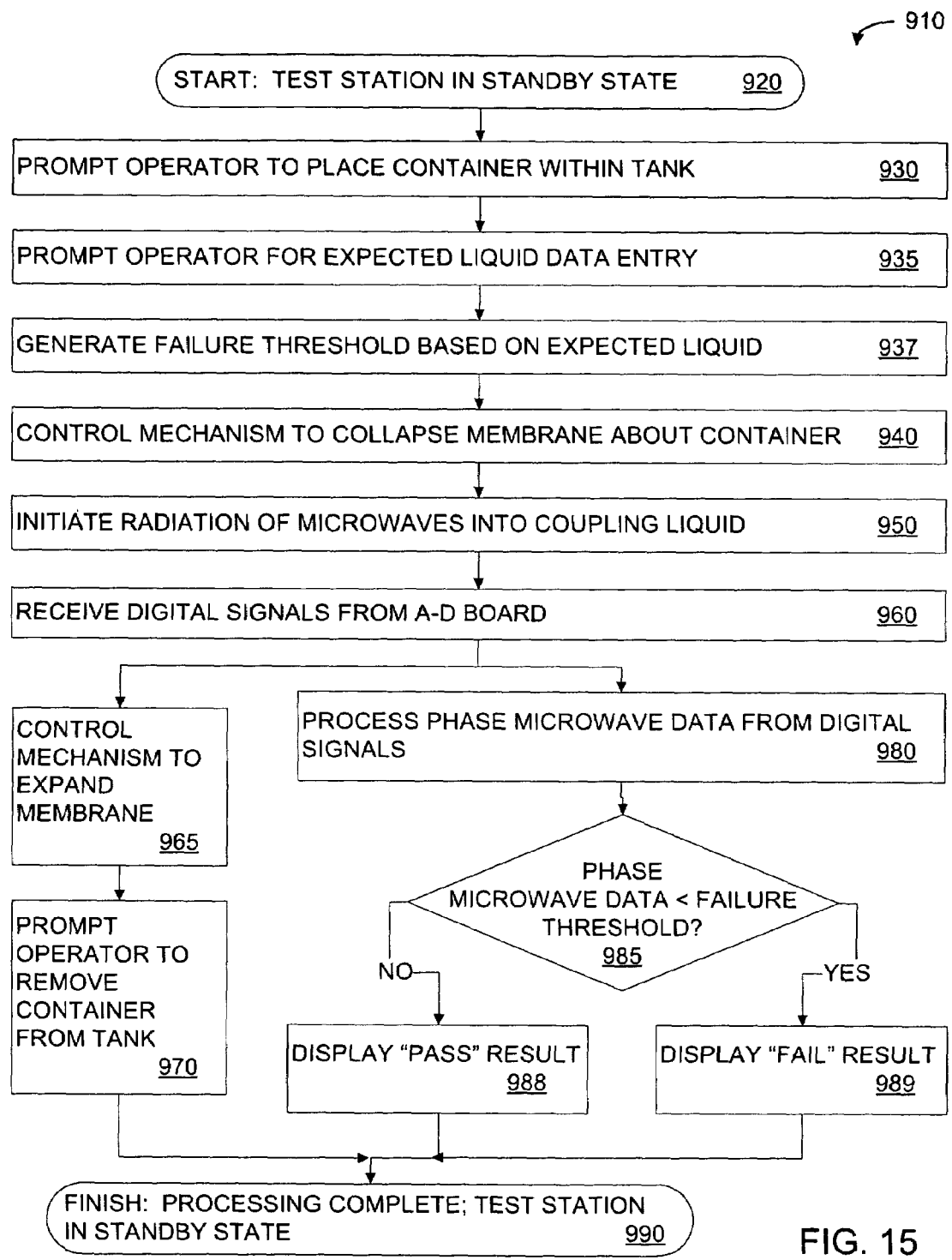
FIG. 15 is a flowchart of another non-invasive microwave analysis process, in accord with an embodiment.

FIG. 15 is a flowchart of a non-invasive microwave analysis process 910. Process 910 may be performed, for example, by a processor of a non-invasive microwave analysis system (e.g., by processor 88 (FIG. 3) of non-invasive microwave analysis system 10 (FIG. 1)). In step 920, a test station is in a standby state such that a tank of the test station (e.g., any of tanks 12, 112, 512, 312 or 412) is available to accept a container for analysis. Step 930 prompts an operator to place the container within the tank. Step 935 prompts the operator for data entry concerning the expected liquid; step 937 generates a failure threshold based on the expected liquid (e.g., by utilizing a look-up table). Step 940 controls a mechanism that collapses a membrane that separates the container from the coupling liquid about the container so that testing may proceed (e.g., processor 88 controls a pump 54 that pressurizes coupling liquid 14, see FIG. 6A and FIG. 6B, or processor 88 controls a motor that manipulates a base 517 on which the container rests, see FIG. 8A and FIG. 8B). Step 950 controls transmission of microwave radiation (e.g., controls power and/or connections of RF source 62 to generate a signal that a transmitter antenna 20 or 720 transmits as microwave radiation) into the coupling liquid. Step 960 receives digital signals corresponding to down-converted IF signals from an A–D board, corresponding to: (a) antennas 30 or 730 converting scattered microwave radiation to microwave electronic signals, (b) receiver modules 78 processing the microwave electronic signals into down-converted IF signals, and (c) A–D board 84 digitizing the down-converted IF signals, as shown in FIG. 3. Step 965 controls a mechanism to expand the membrane to facilitate removal of the container (e.g., processor 88 controls a pump 54 to depressurize coupling liquid 14, see FIG. 6A and FIG. 6B, or processor 88 controls a motor to manipulate a base 517 on which the container rests, see FIG. 8A and FIG. 8B). Step 970 prompts the operator to remove the container from the test station. After step 970, the test station is again in the standby state. As suggested by the branched arrow from step 960 to both of steps 965 and 980, the sequences of (a) steps 965 and 970, and (b) steps 980–989 may be performed in either order (e.g., steps 965 and 970 may be completed first to allow a sample to be physically removed from the test station while processing steps 980–989 occur). Step 980 processes amplitude and phase microwave data from the digital signals. Step 985 compares the phase microwave data with the failure threshold generated in step 937; if the microwave phase data is greater than the failure threshold, step 988 displays a "pass" result; if the microwave phase data is less than the failure threshold, step 989 displays a "fail" result. Process 910 terminates in step 990 with processing complete and the test station in the standby state.

Figure 16:
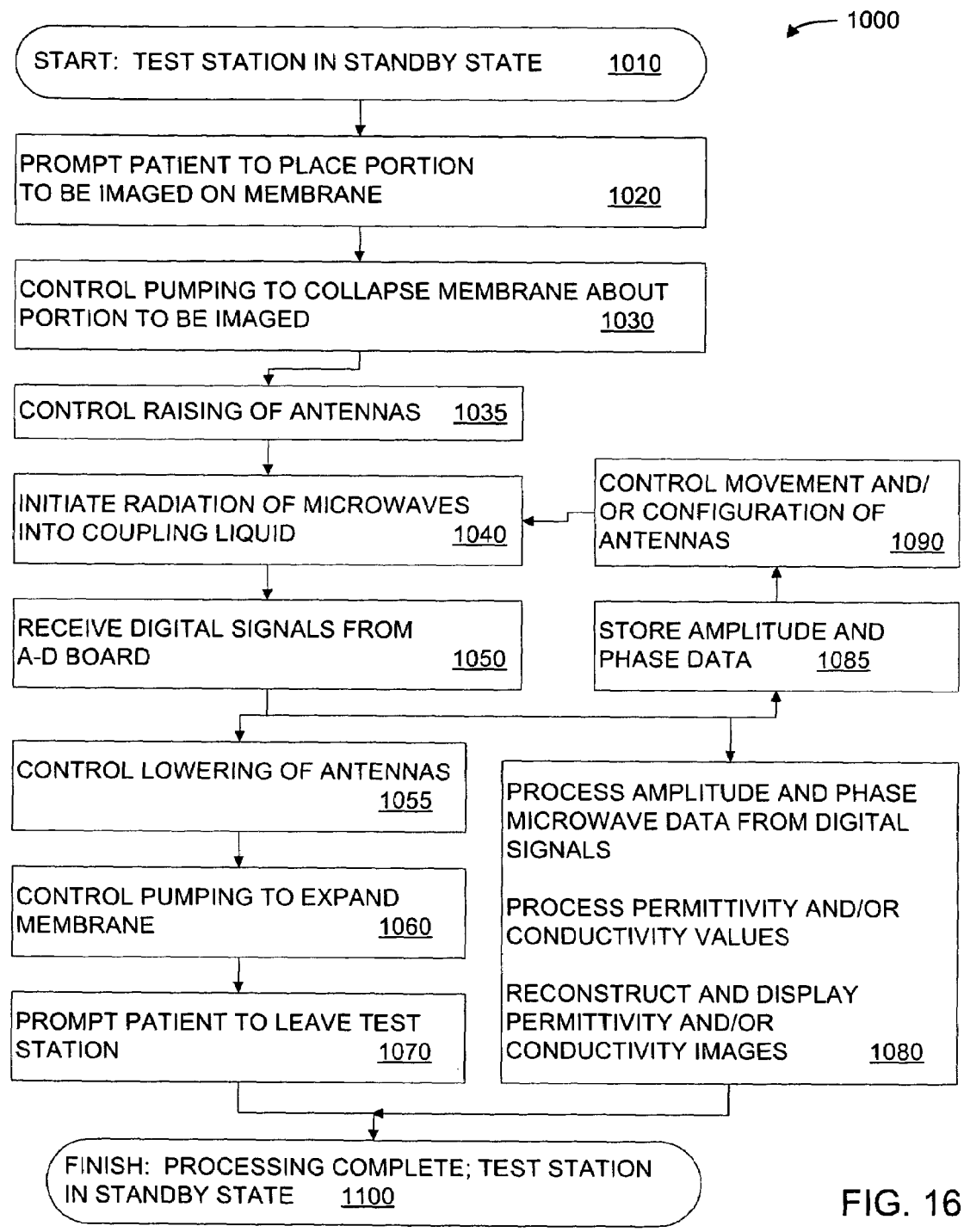
FIG. 16 is a flowchart of another non-invasive microwave analysis process, in accord with an embodiment.

FIG. 16 is a flowchart of a non-invasive microwave analysis process 1000. Process 1000 may be performed, for example, by a processor of a non-invasive microwave analysis system that includes test station 711, to reconstruct images of a portion 3 of a biological subject 5. In step 1010, a test station is in a standby state so that the test station is available to accept a portion for imaging (e.g., portion 3 of subject 5). Step 1020 prompts a patient to place the portion to be imaged on a membrane of the test station. Step 1030 controls pumping to collapse a membrane that separates the portion to be imaged from the coupling liquid about the portion so that testing may proceed (e.g., controls pump 754 to pressurize coupling liquid 14, as described above). Step 1035 controls raising the antennas (e.g., controls a motor raising transmit antenna 720 and receiver antennas 730) so that a plane formed by the antennas intersects a desired image plane within the portion to be imaged. Step 1040 controls transmission of microwave radiation (e.g., controls power and/or connections of RF source 62 to generate a signal that a transmitter antenna 20 or 720 transmits as microwave radiation) into the coupling liquid. Step 1050 receives digital signals corresponding to down-converted IF signals from an A–D board, corresponding to: (a) antennas 30 or 730 converting scattered microwave radiation to microwave electronic signals, (b) receiver modules 78 processing the microwave electronic signals into down-converted IF signals, and (c) A–D board 84 digitizing the down-converted IF signals, as shown in FIG. 3. Step 1055 controls lowering of the antennas (e.g., controls a motor lowering transmit antenna 720 and receiver antennas 730). Step 1060 controls pumping to expand the membrane, to allow removal of the portion being imaged (e.g., controls pump 754 to depressurize coupling liquid 14). Step 1070 prompts the patient to leave the test station. After step 1070, the test station is again in standby state. As suggested by the branched arrow from step 1050 to both of steps 1055 and 1080, the sequences of (a) steps 1055, 1060 and 1070, and (b) step 1080 may be performed in either order (e.g., steps 1055, 1060 and 1070 may be completed first to allow a subject to be physically removed from the test station while processing step 1080 occurs). Step 1080 processes amplitude and phase microwave data from the digital signals, processes permittivity and/or conductivity values, and reconstructs permittivity and/or conductivity images. Optionally, amplitude and phase data may be stored in step 1085, and the movement of the antennas may be controlled (e.g., to raise or lower the antennas, or to change a configuration of transmitter and/or receiver antennas) in step 1090. If images of multiple planes are desired, step 1080 includes associating each height at which antennas are positioned in step 1090, with microwave data taken at each height. Process 1000 terminates in step 1100 with processing complete and the test station in a standby state.

The steps listed in process 1000 are intended to be exemplary; it will be appreciated that certain steps of process 1000 may be performed differently, performed in a different order, or omitted without departing from the scope and spirit hereof. For example, if only one image of a single plane is desired, steps 1085 and 1090 may be omitted. If a test station does not lower antennas when entering a standby state, steps 1035 and 1055 may be omitted.

The changes described above, and others, may be made in the non-invasive microwave analysis system described herein without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A non-invasive microwave analysis method for imaging a portion of a biological subject, comprising:
    transmitting microwave radiation from a transmitter antenna situated within coupling liquid separated from the subject by a flexible membrane;
    converting microwave radiation scattered from the subject into microwave electronic signals at one or more receiver antennas within the coupling liquid; and
    processing the microwave electronic signals to reconstruct a cross-sectional image of the subject.

2. The method of claim 1, wherein the transmitting, converting, and processing steps are repeated at a plurality of antenna positions, relative to the subject, to reconstruct a cross-sectional image of the subject at each of the positions.

3. The method of claim 1, wherein the cross-sectional image is one of a permittivity image and a conductivity image.

4. The method of claim 1, further comprising placing the portion of the subject in a tank that holds the coupling liquid such that the membrane surrounds at least part of the container.

5. The method of claim 4, the step of placing comprising pushing the portion of the subject downwards on a top surface of the membrane.

6. The method of claim 4, further comprising collapsing the membrane about at least part of the portion of the subject.

7. The method of claim 6, the step of collapsing comprising one of pumping additional coupling liquid into the tank and raising a base on which the portion of the subject is placed.

* * * * *